US00PP17824P2

(12) United States Plant Patent
Doguet et al.

(10) Patent No.: US PP17,824 P2
(45) Date of Patent: Jun. 26, 2007

(54) ZOYSIAGRASS PLANT NAMED 'Y2'

(50) Latin Name: *Zoysia japonica*
Varietal Denomination: Y2

(76) Inventors: David Doguet, 1602 Continental, Pleasanton, TX (US) 78064; Virginia Lehman, 811 Mountain River Dr., Lebanon, OR (US) 97355

( * ) Notice: Subject to any disclaimer, the term of this patent is extended or adjusted under 35 U.S.C. 154(b) by 0 days.

(21) Appl. No.: 11/331,614

(22) Filed: Jan. 17, 2006

(51) Int. Cl.
*A01H 5/00* (2006.01)

(52) U.S. Cl. ..... Plt./390
(58) Field of Classification Search ..... Plt./390
See application file for complete search history.

*Primary Examiner*—Kent Bell
*Assistant Examiner*—Annette H Para

(57) ABSTRACT

An asexually reproduced variety of perennial zoysiagrass with a unique combination of morphological characters including medium leaf blade width and good persistence under low maintenance.

2 Drawing Sheets

Latin name of the genus and species of the plant claimed: The present invention relates to the genus and species *Zoysia japonica* (L.) Merr.
Variety denomination: 'Y2'.

BACKGROUND OF THE INVENTION

Field of Invention

The present invention relates to a new and distinct asexually reproduced variety of perennial zoysiagrass (*Zoysia japonica* (L.)) Merr.

BRIEF SUMMARY OF THE INVENTION

BACKGROUND OF THE INVENTION

This invention relates to a new and distinct perennial zoysiagrass cultivar identified as 'Y2' zoysiagrass (herein referred to as 'Y2'). The inventors, David L. Doguet and Virginia G. Lehman, discovered 'Y2' under cultivated conditions near Poteet, Tex. in a collection of plants from Kobe, Japan made by Jack Murray (deceased). 'Y2' was identified as a distinctly different vegetative patch or clonal plant differing by non-aggressiveness and quality under low maintenance from the surrounding plants. The inventors asexually reproduced 'Y2' by taking vegetative cuttings of stolons and rhizomes, cutting the rhizomes and stolons into segments, each with a vegetative bud, and rooting them in potting media.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is Zoysiagrass plant named 'Y2'.

BRIEF DESCRIPTIONS OF THE ILLUSTRATIONS

Figure 1:
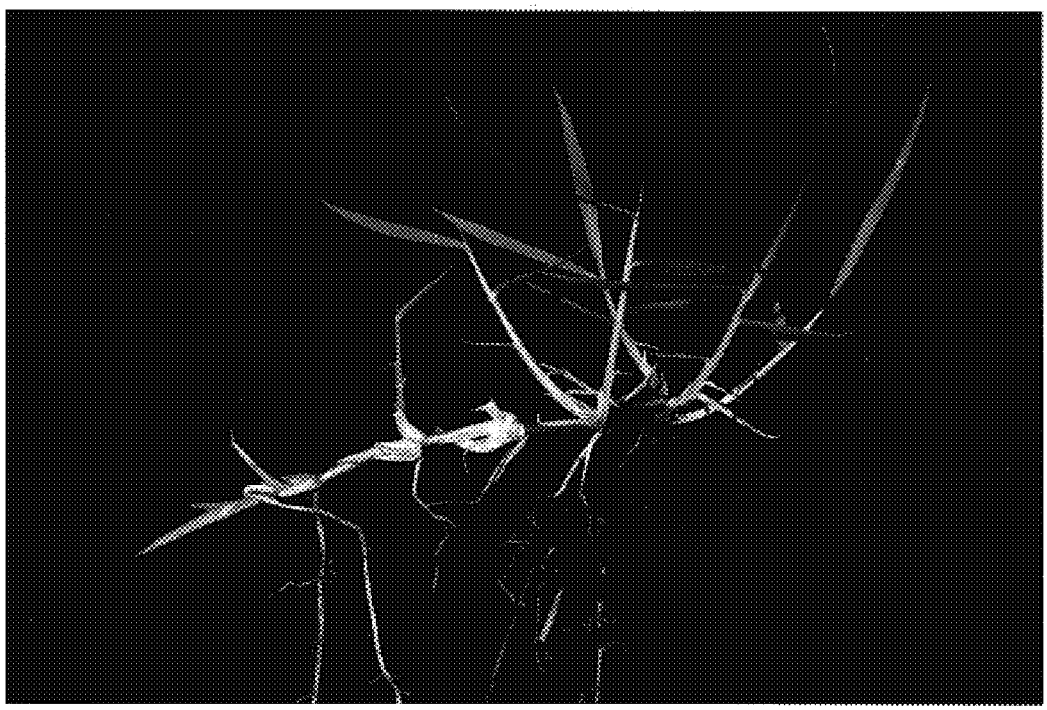

FIG. 1. Plant of 'Y2' zoysiagrass showing stolon and tiller growth.

Figure 2:
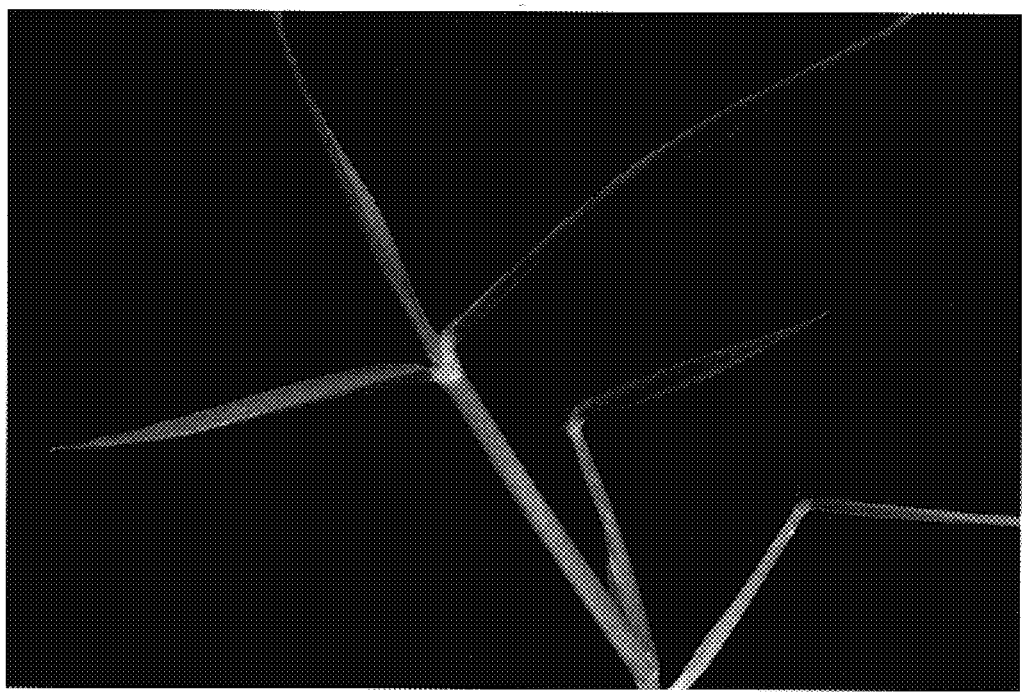

FIG. 2. Tiller of 'Y2' zoysiagrass showing few long leaf hairs.

COMPLETE DESCRIPTION OF THE VARIETY

'Y2' was characterized in greenhouse and field conditions. 'Y2' is a unique variety of zoysiagrass (*Zoysia japonica* (L.)) Merr. that Doguet and Lehman discovered under cultivated conditions near Poteet, Tex. Plants were grown from a collection of plants made by Jack Murray (deceased) from Kobe, Japan. 'Y2' was identified as a distinctly different vegetative patch or clonal plant differing in non-aggressiveness and quality under low maintenance from the surrounding plants. The plants were located in USDA Plant Hardiness Zone 8. 'Y2' was propagated by the inventors under field and greenhouse conditions by cutting of rhizomes and stolons, rooting them in soil, and planting of the rooted material to provide planting stock for studying performance and for comparison of morphological characters after propagation. 'Y2' has been propagated by rhizomes, stolons, tillers, and sod. Asexually reproduced plants of 'Y2' have remained stable and true to type through successive generations of propagation. No seedling establishment from 'Y2' has been noticed in either greenhouse or field studies.

'Y2' is a perennial zoysiagrass that spreads by both stolons and rhizomes. Characteristics of 'Y2' measured in 2005 were taken from plants that were approximately 15 months in age. The greenhouse was located near Lebanon, Oreg., with a nighttime low temperature of 50 degrees F., and daytime high of 80 degrees F., and a minimum soil temperature of 77 degrees F. The plants were grown with a minimum 14-hour day length, supplemented with photosynthetically active radiation equivalent to approximately 50% sunlight. The plants were fertilized with the equivalent of 1 pound of actual N per month, using a soluble fertilizer of 20-20-20 in two equal soluble applications per month.

'Y2' has a stiff leaf of medium length and medium width. 'Y2' has a shorter leaf than Crowne or BM230 (Table 1) when measured under greenhouse conditions in Lebanon, Oreg., 2005. 'Y2' has a longer floral area than 'Diamond' but a shorter floral area than Crowne or BM230 (Table 2). 'Y2' has few adaxial surface leaf hairs compared to the varieties 'Cavalier', 'Palisades', 'Zorro', or 'Crowne' that have many leaf hairs present (Table 3). No seeds of 'Y2' have developed; no seedlings have been noted in field production area or field test areas. The inflorescences produced in the greenhouse have consisted of empty glumes.

'Y2' has not shown susceptibility to the zoysiagrass mite in Poteet, Tex., where some susceptible varieties have shown symptoms of the mite. 'Y2' has shown some susceptibility to cool-weather brown patch. 'Y2' has shown resistance to Fall armyworm when adjacent *Paspalum* and *Cynodon* sp. plants have shown severe damage. 'Y2' has shown to excel with low maintenance inputs and is especially adaptable to areas such as bunker faces. 'Y2' has shown good turfgrass performance and temperature adaptation when tested as far north as Beltsville, Md., USDA hardiness zone 7a, which would extend the area of adaptation for 'Y2' in a line from northern Maryland across central Tennessee through northern Arkansas through Oklahoma in an East/West line and on a North/South line from Washington D.C., south through Mexico. 'Y2' will be limited only by winter survival in colder regions. 'Y2' is superior in survival under low maintenance conditions compared to 'Zeon' and 'Jamur' in water use demands as shown in test situations near Poteet, Tex., and will be limited by adequate precipitation in drier to arid regions. 'Y2' is adapted from sandy to heavier loam soil textures and from slightly acid to slightly alkaline soil pH.

TABLE 1

Leaf blade widths and lengths and texture class of selected zoysiagrass cultivars, measured under greenhouse conditions in Lebanon, OR, 2005.

| Variety | Leaf Stiffness | Length, 4th youngest crown leaf cm | Width, 4th youngest crown leaf mm | Leaf Texture Class |
|---|---|---|---|---|
| 'Y2' | Very Stiff | 1.27 | 1.56 | Medium |
| 'Royal' | Medium Stiff | — | 0.78 | Very Fine |
| 'Diamond' | Soft | 0.85 | 0.92 | Very Fine |
| 'Cavalier' | Medium Stiff | — | 0.55 | Very Fine |
| 'Cavalier' | Medium Stiff | 3.39 | 3.01 | Medium-Coarse |
| BM 230 | Medium Stiff | 2.33 | 3.28 | Coarse |

TABLE 2

Inflorescence and leaf characters of selected zoysiagrass cultivars, measured under greenhouse conditions in Lebanon, OR, 2005.

| Variety | Length floral area cm | Length, flowering stem, from lowest node to base floral region mm | Sheath length, 4th crown leaf cm | Anther length mm | Stem width at base of inflorescence mm |
|---|---|---|---|---|---|
| 'Y2' | 1.67 | 3.7 | 1.55 | 1.16 | 0.81 |
| 'Cavalier' | — | — | 1.25 | — | — |
| 'Diamond' | 1.3 | — | 0.9 | — | — |
| 'Royal' | — | — | 1.43 | — | — |
| 'Palisades' | — | — | 4.15 | — | — |
| 'Crowne' | 3.05 | 11.0 | 3.05 | — | 0.71 |
| 'BM230' | 2.73 | 14.75 | 1.75 | 1.74 | 0.84 |

TABLE 3

Adaxial leaf hair length measurements of selected zoysiagrass cultivars, measured under greenhouse conditions in Lebanon, OR, 2005.

| Variety | Leaf hair, adaxial Presence/ Number |
|---|---|
| 'Y2' | Few |
| 'Palisades' | Many |
| 'Zorro' | Many |
| 'Diamond' | Absent |
| 'Royal' | Absent |
| 'Crowne' | Many |
| 'Cavalier' | Many |
| 'BM230' | Absent |

TABLE 4

Stolon characters of selected zoysiagrass cultivars, measured under greenhouse conditions in Lebanon, OR, 2005.

| Variety | Thickness 1st youngest stolon node mm | Thickness 2nd youngest stolon node mm | Stolon Internode length, 1st to 2nd node cm | Stolon Internode length, 2nd to 3rd node cm | Stolon Internode length, 3rd to 4th node cm |
|---|---|---|---|---|---|
| 'Y2' | 1.56 | 1.96 | 1.03 | 1.06 | 1.13 |
| 'Cavalier' | 1.94 | 2.05 | 2.8 | 2.55 | 2.45 |
| 'Diamond' | 0.88 | 1.16 | 1.27 | 1.5 | 1.34 |
| 'Zorro' | 1.67 | 2.03 | 2.32 | 2.43 | 2.76 |
| 'Royal' | 1.65 | 1.84 | 2.1 | 2.28 | 2.17 |
| 'Palisades' | 2.05 | 2.19 | 2.93 | 4.28 | 5.35 |
| 'Crowne' | 2.13 | 2.27 | 3.2 | 2.43 | 2.95 |
| 'BM 230' | 2.05 | 2.24 | — | — | — |

COMPLETE BOTANICAL DESCRIPTION OF THE VARIETY

Origin: 'Y2' is a cultivar of a single clone discovered under cultivated conditions in a Poteet, Tex. planting of zoysiagrass clones derived from a collection of zoysiagrasses from Kobe, Japan made by Jack Murray (deceased).

Classification: *Zoysia japonica* (L.) Merr.

Growth habit: 'Y2' is a perennial plant that spreads by stolons and rhizomes and produces a dense, fine textured turfgrass. The inflorescence of 'Y2' is a terminal spike-like raceme, with spikelets on short pedicels.

Leaf blade: Rolled in the bud, concave surface.

Leaf blade pubescence: 1 to 25 hairs on adaxial surface, none on abaxial surface.

Leaf sheath pubescence: Absent, except for a few long hairs at mouth of sheath, mean length sheath hairs: Y2: 3.41 mm; Zorro: 4.47 mm; Cavalier: 4.41 mm; BM 230: 5.68 mm; Royal: 4.33 mm; Palisades: 3.51 mm.

Leaf blade margin: Y2=semi-rough; BM230=rough; Cavalier=mostly smooth.

Leaf blade veins: Obscure.

Leaf blade flexibility (softness): Very stiff.

Vegetative leaf, 2nd youngest vegetative leaf, non-flowering stolon:

*Blade length range.*—Y2: 0.7 cm to 2.3 cm, mean length: 1.74 cm; Zorro: 0.3 to 3 cm, mean length: 1.78 cm; Royal: 0.5 to 2.4 cm, mean length: 1.23; Palisades: 1.4 to 11.7 cm, mean length: 7.62 cm.

*Blade width mean.*—Y2: 1.28 mm to 2.4 mm, mean width: 2.09 mm; Zorro: 0.97 to 2.24 mm, mean width: 1.76; Royal: 1.06 to 2.1 mm, mean width: 1.63; Palisades: 2.9 mm to 5 mm, mean width: 3.91.

Sheath length mean, $4^{th}$ youngest vegetative leaf: Range: 0.9 to 2.8 cm, mean length: 1.55 cm; mean, Cavalier: 1.25.

Stolon leaf angle, third youngest leaf: Y2: 78.3; Zorro: 71.4; Cavalier: 80.8; Crowne: 109; BM230: 91.5.

Inflorescence characters:

*Culm total length, including floral area to node below flag leaf.*—5.3 cm. Length of stem of inflorescence: Y2: 3.7 cm. Floral area length: Y2: 1.67 cm; BM230: 2.73 cm.

*Culm width, stem thickness, base of floral area.*—0.57 mm.

*Anther length.*—1.16 mm.

*Floret (seed) length.*—2.54 mm.

*Floret (seed) width.*—0.91 mm.

*Node thickness, node below inflorescence.*—Y2: 0.98 mm; BM230: 1.21 mm.

*Pedicel length.*—1.16 mm.

*Flag leaf length.*—Y2: 0.3 cm; Crowne: 1.53 cm.

*Flag leaf width.*—0.57 mm; Crowne: 1.41 mm.

Mature plant height, including inflorescence: Y2: 4.89 cm; Crowne: 14.6 cm; BM230: 22 cm;

Color notations, vegetative characters, based on The R.H.S. Colour Chart (light quality, photoperiod, and general growth of the plants affect color notations):

*Leaf blade color adaxial leaf surface.*—137 C green.

*Leaf blade color abaxial leaf surface.*—146A yellow green.

*Stolon color.*—145A yellow green; with cool temperatures, will show anthocyanin Purpling, 67A red purple.

Color notations, floral characters, based on The R.H.S. Colour Chart (light quality, photoperiod, and general growth of the plants affect color notations):

*Culm stalk.*—137C green.

*Stigma.*—155A white.

*Anthers, fresh.*—N77A purple.

*Anthers, mature, dried.*—N199D grey brown.

References Cited

| U.S. Patent Documents | | |
|---|---|---|
| October, 1998. | Engelke, M. C. | U.S. PP 10,636. 'Diamond' zoysiagrass |
| October, 2000. | Engelke, M. C. | U.S. PP 11,570. 'Crowne' zoysiagrass |
| December, 1986. | Youngner, V. B. | U.S. PP 5,845. 'El Toro' zoysiagrass |
| September, 2000. | Engelke, M. C. | U.S. PP 11,515. 'Palisades' zoysiagrass |

We claim:

1. A new and distinct variety of zoysiagrass plant, substantially as described and illustrated herein, characterized particularly by a unique combination of morphological characters.

* * * * *